United States Patent [19]

Nakayama et al.

[11] Patent Number: 5,234,828

[45] Date of Patent: Aug. 10, 1993

[54] PROCESS FOR PRODUCING NOVEL HEAT-RESISTANT β-GALACTOSYLTRANSFERASE

[75] Inventors: Toru Nakayama, Ikeda; Yukiko Kodama, Takatsuki; Norihide Amano, Takatsuki; Masahiro Nakao, Takatsuki; Yuji Shibano, Toyonaka; Teruo Amachi, Takarazuka, all of Japan

[73] Assignee: Suntory Limited, Osaka, Japan

[21] Appl. No.: 907,639

[22] Filed: Jul. 2, 1992

Related U.S. Application Data

[62] Division of Ser. No. 669,574, Mar. 14, 1991, Pat. No. 5,153,128.

[30] Foreign Application Priority Data

Mar. 16, 1990 [JP] Japan .................................. 2-64318
Sep. 17, 1990 [JP] Japan ................................ 2-246792

[51] Int. Cl.$^5$ ......................... C12N 9/10; C12N 9/38; C12R 1/01
[52] U.S. Cl. ........................................ 435/193; 435/97; 435/99; 435/207; 435/252.1; 435/822
[58] Field of Search ................ 435/97, 99, 193, 252.1, 435/207, 822

[56] References Cited

U.S. PATENT DOCUMENTS 4,590,160  5/1986  Nishihashi et al. .................... 435/97
5,153,128  10/1992  Nakayama ........................... 435/193

FOREIGN PATENT DOCUMENTS 279778   2/1988  European Pat. Off. .
323201  12/1988  European Pat. Off. .

OTHER PUBLICATIONS

World Patent Index Latest Derwent Abstract 83-708567 [28], Derwent Publications Ltd., JP 58094367 (Dainippon Ink Chem KK et al.) Jun. 4, 1983.
World Patent Index Derwent Abstract No. 87-012547 [02] Derwent Publications Ltd., JP 61271999 (Nisshin Seito KK) Dec. 2, 1986.
World Patent Index Latest Derwent Abstract 86-321500 [49] Derwent Publications Ltd., JP 61236790 (Nisshin Seito KK) Oct. 22, 1986.
World Patent Index Latest Derwent Abstract No. 86-014446 [03], Derwent Publications Ltd., 227449 (AKAD Wissenschaft DDR) May, 18 1985.
Patent Abstracts of Japan, vol. 13, No. 11 (558) Jan. 11, 1989; and JP A 63219399 (Unitaka Ltd) Sep. 13, 1988.

Primary Examiner—Herbert J. Lilling
Attorney, Agent, or Firm—Oblon, Spivak, McClelland, Maier & Neustadt

[57] ABSTRACT

Described herein are a novel heat-resistant β-galactosyltransferase, a production process of the enzyme and a utilization method of the enzyme. The enzyme is produced preferably by produced by a microorganism belonging to the family of Actinomycetaceae, which may be selected from fungi belonging to the genus Saccharopolyspora, the genus Thermomonospora or the genus Thermoactinomyces.

2 Claims, 1 Drawing Sheet

PROCESS FOR PRODUCING NOVEL HEAT-RESISTANT β-GALACTOSYLTRANSFERASE

This is a division of application Ser. No. 07/669,574, filed on Mar. 14, 1991, now U.S. Pat. No. 5,153,128.

BACKGROUND OF THE INVENTION

1) Field of the Invention

This invention relates to a novel heat-resistant β-galactosyltransferase, its production process and its use. More specifically, this invention is concerned with a novel β-galactosyltransferase produced by a microorganism belonging to the family of Actinomycetaceae—such as a microorganism belonging to the genus Saccharopolyspora—and having high heat stability, its production process and its use.

2) Description of the Related Art

Modification of a saccharide or glycoside by glycosylation is known to make it possible to impart new physiological activities or physical properties to the first-mentioned saccharide or glycoside (hereinafter simply called a "saccharide"). For example, such modification is known to enhance sweetness, to reduce or eliminate bitterness, to increase the water solubility of glycosides having low solubility in water (illustrative examples are found among active ingredients of Chinese herbal remedies and like ingredients), and/or to improve in vivo stability and intestinal absorption.

A function imparted as a result of glycosylation and its degree vary depending on the type of the glycosyl donor and also the nature of the saccharide so modified. There have however been many reports in which preferable results are obtained for the above-mentioned objects by modifying saccharides with galactosyl groups. Based on such reports, a variety of function oligosaccharides and function glycosides have been increasingly developed.

For example, among oligosaccharides or saccharide-modified glycosides represented by the following formula:

Gal—(Gal)$_m$—X in which Gal means a galactosyl group, X denotes a saccharide or glycoside and m stands for an integer, oligosaccharides (galactooligosaccharides) in which X is a glucosyl group (Glu) and m is an integer of 0–4 are known as proliferation promoting substances for *Bifidobacterium bifidum*, a benign intestinal bacterium (Japanese Patent Application Laid-Open "Kokai" No. SHO 55-104885). In addition, they are found to have a wide range of utility as food materials for their excellent sweetness intensity and quality, low cariogenecity, low calorific nature, high processing stability, good moisture retaining property, high water-activity lowering ability, good colorability, etc.

Further, galactosylation of sucrose provides galactosylsucrose of the above formula in which X is sucrose and m is 0 (Japanese Patent Application Laid-Open "Kokai" No. SHO 64-85090) whereas galactosylation of lactulose yields galactosyllactulose of the above formula in which X is lactulose and m is 0 (Japanese Patent Application Laid-Open "Kokai" No. SHO 63-94987). These modified saccharides are also found to have new functions as galactooligosaccharide has. In addition, as to the sweet glycoside rubsoside, improvements to its sweetness intensity and quality have been achieved by galactosylation [Argic. Biol. Chem. 53, 2923-2928 (1989)].

As has been described above, the transgalactosylation reaction by β-galactosidase is utilized to add one or more galactosyl groups or oligogalactosyl groups so that a galactosylated product can be produced.

This reaction has its basis on the fact that some β-galactosidases catalyze the β-D-transgalactosylation reaction to a saccharide (or a saccharide moiety of a glycoside) in the presence of β-galactopyranoside at a high concentration.

The levels of the ability of enzymes to transfer a β-galactosyl group vary widely depending on their sources. To make the reaction proceed efficiently, it has been necessary to use a β-galactosidase having high transgalactosylation activity.

Exemplary conventional β-galactosidases include the enzyme derived from the mold fungus, Aspergillus oryzae (Japanese Patent Publication "Kokoku" No. SHO 55-104885), and the enzymes derived from the bacteria, *Bacillus circulans* (Japanese Patent Publication "Kokoku" No. SHO 62-209780) and *Streprococcus thermophilus* [Food Chem. 10, 195–204 (1983)]. Galactooligosaccharide is actually produced by causing these enzymes to act on lactose. Further, examples of yeast cells having β-galactosidase activities including Lipomyces, Rhodotrula, Sirobasidium, Sterigumatomyces (Journal of the Agricultural Chemical Society of Japan, 63(3), 629 (1989)], Sporoboromyces (Japanese Patent Publication "Kokai" No. SHO 62-208293), Cryptococcus (Japanese Patent Publication "Kokai" Nos. SHO 60-251896, SHO 62-130695 and SHO 61-236790), and Kluyveromyces (Japanese Patent Publication "Kokai" No. SHO 61-271999). Production of galactooligosaccharide making use of these yeast cells is also attempted.

Generally, as a donor of β-D-galactosyl groups, use of lactose is most advantageous from the industrial viewpoint. Lactose is contained abundantly in cow milk and is also produced as a dairy waste abundantly in a large volume outside Japan, so that its price is lowest as a raw material. Incidentally, based on the fact that the production of lactose-hydrolyzed milk making use of a β-galactosidase has already been practiced [Food Chemical, 7, 38–44 (1986)], a production process of processed galactooligosaccharide-containing milk, said process making use of a β-galactose having high transfer activity, has been reported recently (Japanese Patent Application Laid-Open "Kokai" No. HEI 1-168234).

In general, a glycosyl transfer reaction proceeds faster and more efficiency as the concentration of a galactosyl donor ("lactose" in the present specification) becomes higher. For this reason, it is desirous to makes the concentration of lactose higher in the reaction mixture. However, a lactose solution of high concentration has high viscosity and tends to permit easy precipitation of crystals at room temperature, leading to the problem that its handling is difficult during the production steps.

It has hence been required to raise the temperature of the reaction system (for example, to 60° C. or higher) so that precipitation of lactose can be suppressed and the viscosity can be lowered. It is advantageous from the standpoint of cost to increase the amount of the reactant (lactose or the like) to be charged per unit volume by increasing its solubility. Further, a chemical reaction proceeds faster as the temperature becomes higher. It is accordingly possible to increase the velocity of the enzyme reaction and hence to shorten the reaction time by raising the temperature of the reaction system. In addition, a higher reaction temperature makes saprophytes difficult to grow. Furthermore, it is also expected that bacteriostatic action takes place by the high osmotic pressure of the resulting high-concentration saccharide solution, said pressure having been achieved by the high temperature, and contributes to the prevention of saprophytic contamination during the production steps.

Although the transgalactosylation reaction at high temperatures has many advantages as has been described, the enzyme is required to have high heat stability in order to conduct the reaction at such a high temperature. Moreover, to advantageously use the above reaction in the industry, it is required to immobilize the enzyme and to make the reaction steps automatic and continuous so that the addition product can be mass produced and its production cost can be lowered.

A β-galactosidase can be stabilized by lactose of high concentration in general. Still higher heat resistance is however required to immobilize the enzyme and to use it repeatedly at high temperatures over a long period of time. The enzymes derived from the mold fungus, *Aspergillus oryzae*, the enzymes derived from the bacteria, *Bacillus circulans* and *Streptococcus thermophilus*, and yeast cells having β-galactosidase activities such as Lipomyces, Rhodotrula, Sirobasidium, Sporoboromyces, Cryprococcus and Kluyveromyces are not sufficiently high in heat stability. Their repeated use at high temperatures is therefore not suitable.

On the other hand, as a β-galactosidase having high heat stability and capable of withstanding repeated use at high temperatures, the enzyme of *Paecilomyces variori* [Appl. Microbiol. Biotechnol., 27, 383-388 (1988)] is known. The optimal reaction pH of this enzyme is however 3.5, so that it is unsuitable for production steps in which lactose contained in cow milk (pH: approx. 7) is utilized.

SUMMARY OF THE INVENTION

There has hence been a demand for the provision of an enzyme suitable for an actual high-temperature enzyme reaction.

The present inventors have searched for enzymes in the nature, which have high β-D-galactosyl group transferring ability and high heat stability and can act in an neutral range. As a result, it has been found that cell strains belonging to the family of Actinomycetaceae, especially, those belonging to the genus Saccharopolyspora, the genus Thermomonospora or the genus Thermoactinomyces include those producing a β-galactosyltransferase which conforms with the above objects.

It has also been found that a heat-resistant β-galactosyltransferase can be used for the production of an oligosaccharide or saccharide-modified glycoside, which is represented by the following formula (I):

Gal—(Gal)$_n$—X (I)

wherein Gal means a galactosyl group, X denotes a saccharide or glycoside and n stands for an integer of 0-4, by subjecting one of these cell strains to liquid culture or solid culture to have the strain produce the heat-resistant β-galactosyltransferase and, if necessary, refining and purifying or immobilizing the same.

The present invention therefore provides a novel heat-resistant β-galactosyltransferase, a production process of the enzyme and a utilization method of the enzyme.

DETAILED DESCRIPTION OF THE INVENTION AND PREFERRED EMBODIMENTS

Figure 1:
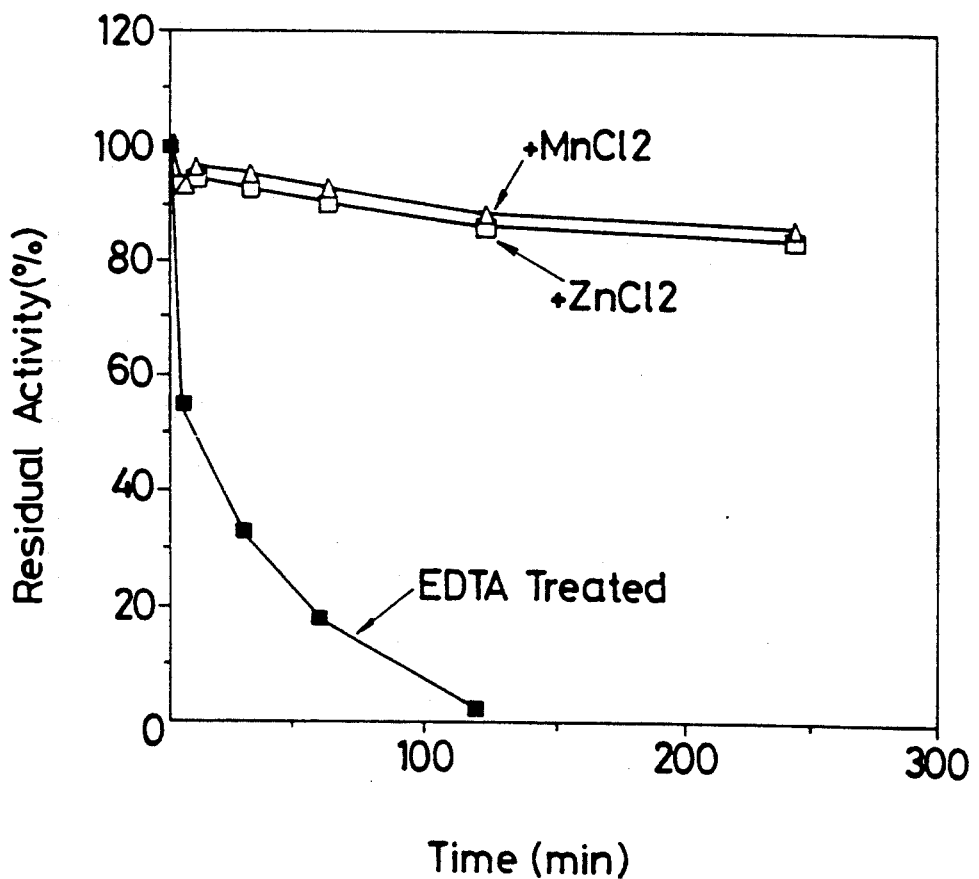
FIG. 1 is a diagram showing effects of manganese and zinc ions to heat stability.

The heat-resistant β-galactosyltransferase according to the present invention can be obtained from a culture of a microorganism belonging to the family of Actinomycetaceae, especially, a cell strain belonging to the genus Saccharopolyspora, the genus Thermomonospora, the genus Thermoactinomyces or the like.

The present inventors, as described above, searched for β-galactosyltransferase-producing microorganisms in nature, which have high heat stability and can act in the neutral pH range. As a result, it was found that the strains belonging to the above family include those producing a heat-resistant β-glactosyltransferase. Of these, an actinomycete strain, SAM 1400, isolated from pastureland soil in Ishikawa-ken, Japan and belonging to the genus Saccharopolyspora produces the intended heat-resistant β-galactosyltransferase in a particularly large amount.

Taking the actinomycete strain, SAM 1400 as a typical example of β-galactosyltransferase-producing fungi useful in the practice of the present invention, its taxonomical characteristics will hereinafter be described.

(1) Morphological appearance:
  SAM 1400 strain forms substrate mycelia and aerial mycelia, whose diameters range from 0.4 μm to 0.8 μm. Substrate mycelia are branched, and rarely separate. Aerial mycelia are branched and form 3-7 and, in some rare occasions, 10 or more long linear spore chains at tips thereof. Even when no aerial mycelia are formed, 2-6 spore chains are formed at substrate mycelia, inside an agar medium, on a surface of the agar medium, and from the surface of the agar medium into the air. Their sizes are 0.8-1.0 μm in diameter, and their surfaces are smooth. Structural elements such as sporangia, mycerial cord or sclerotia were not observed even after cultured for 14 days.

(2) Cultural characterization (cultured at 55° C. for 14 days):
  Sucrose-nitrate agar medium:
    Growth: Poor.
    Aerial mycelia: Not formed.
    Reverse color: Grayish yellow.
    Soluble pigment: None.
  Glucose-asparagine agar medium:
    Growth: Poor.
    Aerial mycelia: Not formed.
    Reverse color: Grayish yellow.
    Soluble pigment: None.
  Glycerin-asparagine agar medium:
    Growth: Abundant.
    . Aerial mycelia: Not formed.
    Reverse color: Pale yellow.
    Soluble pigment: None.
  Starch-inorganic salts medium:
    Growth: Poor.
    Aerial mycelia: Not formed.
    Reverse color: Yellow.
    Soluble pigment: None.

Tyrosine-agar medium:
  Growth: Abundant.
  Aerial mycelia: Not formed.
  Reverse color: Grayish yellow.
  Soluble pigment: None.
Nutrient agar medium:
  Growth: Abundant.
  Aerial mycelia: Slightly formed.
  Reverse color: Yellow.
  Soluble pigment: None.
Yeast extract-malt extract agar medium:
  Growth: Abundant.
  Aerial mycelia: Poor, white.
  Reverse color: Yellowish brown.
  Soluble pigment: None.
Oat meal agar medium:
  Growth: Abundant.
  Aerial mycelia: Not formed.
  Reverse color: Yellow.
  Soluble pigment: None.
NaCl-agar medium*
  Growth: Abundant.
  Aerial mycelia: Abundant, white
  Reverse color: Yellow.
  Soluble pigment: None.
* Tripticase soy broth (BBL) containing 10% NaCl+2% agar medium.

(3) Physiological characterization:
  i) Growth temperature range: Growth was observed at 50° C., 55° C. and 65° C. on nutrient agar medium containing 1% of glucose and also at 30° C. and 37° C. on tripticase soy broth (BBL)+2% agar medium. The optimal growth temperature therefore appeared to be 50°–55° C.
  ii) Liquefaction of gelatin (55° C.): Growth was not observed on any one of the media used for the gelatin liquefaction test.
  iii) Hydrolysis of starch: Negative.
  iv) Coagulation of skim milk: Negative.
  v) Peptonization of skim milk: Negative.
  vi) Formation of melanin-like pigment:
    Peptone-yeast extract-iron agar medium: Negative*.
    Tyrosine agar medium: Negative.
    Tripton-yeast extract agar medium: Negative.
* Settling of a pale brown pigment was observed in the bottom of the medium.
  vii) Reduction of nitrates: Positive.
  viii) 10% NaCl resistance: Positive.
  ix) Decomposition of guanine: Positive.
  x) Decomposition of elastin: Negative.
  xi) Decomposition of xanthine: Positive.
  xii) Decomposition of hypoxanthine: Positive.
  xiii) Assimilation of carbon sources (cultured at 55° C. for 17 days on Pridham-Gottlieb agar medium):

| | |
|---|---|
| D-Glucose | + |
| D-Xylose | + |
| Lactose | + |
| L-Rhamnose | ± |
| L-Arabinose | ± |

-continued

| | |
|---|---|
| D-Fructose | + |
| Raffinose | − |
| D-Mannitol | + |
| Inositol | + |
| Sucrose | − | wherein +: assimilable, ±: assimilation is doubtful, −: not assimilable.

(4) Chemolaxonomic properties:
  a) 2,6-Diaminopimelic acid: Whole cells were investigated in accordance with the method proposed by Staneck, J. L. and Roberts, G. D. in Applied Microbiology, 28, 226 (1974). As a result, the existence of meso-2,6-diaminopimellic acid was confirmed.
  b) Sugars: The existence of araminose and galactose was observed in a hydrolysate of whole cells.
  c) Quinones Contained MK-9(H4) as a principal component. Also contained were MK-9(H6), MK-9(H8), MK-10(H4), MK-10(H6), MK-10(H8) and MK-10(H10).
  d) Phospholipid type: Phosphatidylcholine and phosphatidylglycerol are present. This means that the phospholipid type is P-III type as proposed by Lechevalier, M. P. and Lechevalier, H. A. (compiled Dietz, A. and Thayer, D. W.) in Actinomycete Taxonomy, 227–291 (1980).
  e) Mycolic acid: No mycolic acid is contained within the cells.

From these results, cell walls of SAM 1400 strain is found to be of IV-A type which contains meso-2,6-diaminopimellic acid, galactose and arabinose.

As morphological characteristics, SAM 1400 strain forms aerial mycelia, and branched, smooth and spherical spores are adhered on chains. Spore chains are short. There are 3–7 spore chains usually, but 10 or more spore chains may be observed in rare occasions. When formation of aerial mycelia was not observed on the other hand, formation of spore chains was observed on substrate mycelia. Each spore chain consisted of 2–6 smooth spherical spores located from a substrate mycelium to a tip of a short sporophore (this may not be observed in some instances) and extends upwardly from the surface of the agar medium. Quinones include MK-9(H4) as a principal component, the phospholipid type is P-III, and no mycolic acid is contained. Decomposes guanine, hypoxanthine and xanthine but does not decompose elastin. Grows at 30°–65° C. and shows resistance to 10% NaCl.

Based on the above mycological characteristics, the taxonomic position of the strain was determined in accordance with Williams, S. T. (ed.), Bergey's Manual of Systematic Bacteriology, vol. 4 (1989). SAM 1400 strain was found to be an actinomycete belonging to the genus *Faenia rectivirgula*.

The type strain of F. rectivirgula and two strains identified as *F. rectivirgula* were compared with SAM 1400 strain in cultural characteristics, physiological properties and quinones. The results are shown in Table 1.

TABLE 1

| | Strain | | | |
|---|---|---|---|---|
| Characteristics | SAM 1400 | F. rectivirgula JCM-3057 | F. rectivirgula JCM-3099 | F. rectivirgula JCM-3034 |
| Aerial mycelium forming ability | Poor, but promoted by 10% NaCl addition. | Poor, but promoted by 10% NaCl addition. | Poor, but promoted by 10% NaCl addition. | Poor, but promoted by 10% NaCl addition. |

TABLE 1-continued

| Characteristics | SAM 1400 | F. rectivirgula JCM-3057 | F. rectivirgula JCM-3099 | F. rectivirgula JCM-3034 |
|---|---|---|---|---|
| Color tone of aerial mycelia | White | White | White | White |
| Production of soluble pigment | − | − | − | − |
| Growth in the presence of 10% NaCl | + | + | + | + |
| Growth at 30° C. | + | + | − | + |
| Growth at 65° C. | + | + | + | − |
| Decomposition of guanine | + | + | + | − |
| Decomposition of elastin | − | − | − | − |
| Decomposition of xanthine | + | + | + | − |
| Decomposition of hypoxanthine | + | + | + | − |
| Reduction of nitrate salt | + | + | + | + |
| Coagulation and peptonization of milk | − | − | − | − |
| Decomposition of starch | − | − | − | − |
| Liquefaction of gelatin | No growth | No growth | No growth | − |
| (Assimilation of carbon sources) | | | | |
| D-Glucose | + | + | + | + |
| D-Xylose | + | + | + | ± |
| Lactose | + | + | + | − |
| L-Rhamnose | ± | − | ± | − |
| L-Arabinose | ± | − | ± | − |
| D-Fructose | + | + | + | + |
| Raffinose | − | − | − | − |
| D-Mannitol | + | + | + | + |
| Inositol | + | + | + | + |
| Sucrose | − | − | − | − |
| (Composition of menaquinone*) | | | | |
| MK-9 (H4) | ++ | +++ | ++ | +++ |
| MK-9 (H6) | + | + | + | + |
| MK-9 (H8) | + | − | + | Trace |
| MK-10 (H4) | + | + | + | − |
| MK-10 (H6) | + | + | + | − |
| MK-10 (H8) | + | − | + | − |
| MK-10 (H10) | Trace | − | + | − |

*The proportions (%) of the menaquinones contained are shown in accordance with the following four-stage system:
Trace: <3%,
+: 3–14%,
++: 15–49%,
+++: >50%.

As is shown in Table 1, SAM 1400 strain and the three strains of F. rectivirgula, including the type strain thereof, showed toxomical properties which conformed very well.

From the foregoing, the present inventors identified SAM 1400 strain as F. rectivirgula. However, Korn-Wendisch et al. identified the genus Faenia as identical to the genus Saccharopolyspora by their chemical taxonomic properties such as the compositions of cellular fatty acids, their quinones and their phospholipid types, moved F. rectivirgula to the genus Saccharopolyspora and proposed the new combination, Saccharopolyspora rectivirgula [International Journal of Systematic Bacteriology, 39, 430–441 (1989)].

Accordingly, the present inventors identified the present cell strain as Saccharopolyspora rectivirgula in accordance with the proposal by Korn-Wendisch et al. [International Journal of Systematic Bacteriology, 39, 430–441 (1989)].

Incidentally, SAM 1400 strain has been named Saccharopolyspora rectivirgula SAM 1400 and deposited under FERM BP-2768 with Fermentation Research Institute, Agency of Industrial Science and Technology, Ministry of Industrial Trade and Industry, Government of Japan.

Examples of novel β-galactosyltransferase-producing actinomycetes, which belong to other genera respectively, include Thermoactinomyces sp. SAM 1544, Thermoactinomyces sp. SAM 1545, Thermomonospora sp. SAM 1546 and Thermomonospora sp. SAM 1547.

These actinomycetes have also been deposited under FERM BP-2769, FERM BP-2770, FERM BP-2771 and FERM BP-2772, respectively, with Fermentation Research Institute, Agency of Industrial Science and Technology, Ministry of Industrial Trade and Industry, Government of Japan.

Production of the novel β-galactosyltransferase making use of one of the above actinomycetes is conducted by inoculating the actinomycete to a culture medium and then culturing the actinomycete in a manner known per se in the art.

Culture of each cell strain can be effected by conventional liquid culture or solid culture such as aerated-stirring culture, shake culture or standing culture.

The culture medium contains lactose, glucose, sucrose and/or starch as carbon sources, peptone, yeast extract, urea, ammonium sulfate and/or amino acids as nitrogen sources, and potassium phosphate, magnesium sulfate, calcium chloride and/or the like as inorganic salts. The culture medium may also be added suitably with trace metals such as $Mn^{2+}$, $Zn^{2+}$, $Ni^{2+}$ and/or the like, vitamins such as biotin and/or thiamine, as needed.

No particular limitation is imposed on the culture temperature as long as it is within a temperature range that permits growth, but 50° C. or so is desirable. The culture is carried out for 24-192 hours or so.

To collect the β-galactosyltransferase of the present invention from the culture thus obtained, the culture is separated into a broth fraction and a cell fraction by centrifugal separation, filtration or the like. Known methods such as ultrafiltration, dialysis, salting-out, solvent precipitation, ion-exchange chromatography, gel chromatography, adsorption chromatography, hydrophobic chromatography and isoelectric precipitation are applied either singly or in combination to the active fraction of the β-galactosyltransferase, whereby a concentrated or purified sample of the β-galactosyltransferase can be obtained.

Of the heat-resistant β-galactosyltransferases of the present invention isolated and purified as described above, the followings are enzymochemical properties of the enzyme produced by Saccharopolyspora rectivirgula a SAM 1400:

Enzymochemical Properties (1) Action
  Transfer reaction:
    Forms 1 mole of a β-D-galactopyranoside Gal-Y and 1 mole of X from 1 mole of another β-D-galactopyranoside Gal-X and 1 mole of a galactosyl group receptor, Y wherein X and Y are both compounds other than water and are each a saccharide or aglycon.
  Hydrolysis:
    Forms 1 mole of X and 1 mole of galactose by hydrolyzing 1 mole of the β-D-galactopyranoside Gal-X.

(2) pH Stability
  After incubated at 55° C. for 15 minutes in 0.01M acetate buffer (pH 3.5-6.5), 0.01M phosphate buffer (pH 6.0-8.0) and 0.01M pyrophosphate buffer (pH 8.0-9.5), the residual activities at the respective pH were measured. As a result, the enzyme was found stable at pH 5.0 and higher.

(3) Heat stability:
  After incubated at 30°-80° C. for 1 hour in 0.01M phosphate buffer (pH 7.2), the residual activities at the respective temperatures were measured. As a result, the enzyme was found substantially stable up to 0° C. In addition, the enzyme was also treated at 65° C. for 24 hours in 0.01M phosphate buffer (pH 7.2) which contained 1M of lactose. The residual activity was then measured. As a result, no inactivation was observed.

(4) Optimal pH:
  The optimal pH in 0.1M phosphate buffer (pH 6.0-8.0) was 7.2.

(5) Substrate specificity:
  Various β-galactopyranosides and their analogous compounds were hydrolyzed at the substrate concentration of 10 mM. The results are summarized in Table 2.

TABLE 2

| Substrate (10 mM) | Relative activity |
| --- | --- |
| p-Nitrophenyl-β-D-galactopyranoside | 100% |
| p-Nitrophenyl-α-D-galactopyranoside | 0% |
| p-Nitrophenyl-β-D-xylopyranoside | <1% |
| p-Nitrophenyl-β-D-glucopyranosise | <1% |
| p-Nitrophenyl-β-D-frucoside | 0% |
| p-Nitrophenyl-β-D-mannoside | 0% |
| Lactose | 161% |

(6) Molecular weight:
  By high performance liquid gel chromatography making use of "TSK-G3000 SW-XL Column" (mobile phase: 0.01M phosphate buffer containing 0.15M KCl, pH 7.2; flow rate: 1.0 ml/min), the molecular weight of the enzyme was determined from its relative elution retention times to those of various standard proteins produced by Oriental Yeast Co., Ltd. The molecular weight of the enzyme was 140,000±20,000.

(7) Molecular weight and structure of subunit:
  The molecular weight of the subunit of the present enzyme was determined as 140,000±20,000 by SDS polyacrylamide gel electrophoresis. Using a Phast-Gel electrophoresis apparatus, the molecular weight of the subunit was determined from its relative migration distances to the various standard proteins. The present enzyme appears to be a monomer.

(8) Inhibitors:
  The present enzyme was inhibited by metal ions, such as $Hg^{2+}$ and $Cu^{2+}$, and ethylenediamine tetraacetate (see Table 3).

TABLE 3

| Compound | Residual activity |
| --- | --- |
| $CdCl_2$ | 96% |
| $ZnCl_2$ | 122% |
| $CaCl_2$ | 87% |
| $BaCl_2$ | 96% |
| $NiCl_2$ | 59% |
| $MnCl_2$ | 103% |
| $CoCl_2$ | 97% |
| $FeCl_2$ | 87% |
| $CuCl_2$ | 28% |
| EDTA | 5% |
| 2-Mercaptoethanol | 96% |
| DTNB | 107% |
| Monoiodoacetic acid | 69% |

(9) Activity measurement:
  Measurement of the hydrolytic activity of p-nitrophenyl-β-D-galactopyranoside was conducted by spectroscopically determining p-nitrophenol formed by the hydrolysis of the substrate.

Namely, 0.10 ml of an enzyme solution was added to 0.60 ml of 0.01M phosphate buffer (pH 7.2) which contained 0.01M of p-nitrophenyl-β-D-galactopyranoside. Increase in absorbance at 405 nm was followed at 55° C. Using the molecular extinction coefficient ($\epsilon_{405}=1.34\times10^4$) of p-nitrophenol at pH 7 2, the amount (μmol) of p-nitrophenol so formed was determined by calculation. One enzyme unit (pNPGU) defined by hydrolysis of p-nitrophenyl-β-D-galactopyranoside is the amount of the enzyme capable of hydrolyzing 1 μmol of p-nitrophenyl-β-D-galactopyranoside within 1 minute. Measurement of the hydrolytic activity of lactose was conducted by spectrophotometrically and quantitatively analyzing glucose formed by the decomposition of the substrate. Namely, 0.10 ml of an enzyme solution was added to 0.90 ml of 0.01M phosphate buffer (pH 7.2) which contained 0.1M of lactose. They were reacted at 55° C. for 10 minutes, followed by the addition of 0.05 ml of 33% trichloroacetic acid to terminate the reaction. To 0.1 ml of the resulting reaction mixture, 1.0 ml of a glucose determination kit (product of Boehringer Mannheim GmbH) was added. After the mixture thus prepared was left over at room temperature for 45 minutes, the absorbance was measured at 660 nm. One enzyme unit (LU) defined by the hydrolysis of lactose is the amount of the enzyme capable of hydrolyzing 1 µmol of lactose within 1 minute.

The β-galactosyltransferase of the present invention has been found novel from the various enzymological properties described above.

The present invention will next be described in further detail by the following examples.

EXAMPLE 1

A culture medium (pH 7.2) containing 3.0% of lactose, 1.4% of "AMINOSAN V3" (beet extract), 0.2% of monosodium glutamate, 0.1% of yeast extract, 0.1% of monopotassium phosphate and 0.05% of magnesium sulfate was placed 100 ml by 100 ml in 500-ml Meyer flasks, followed by sterilization at 120° C. and 1 atm for 15 minutes in an autoclave. SAM 1400 strain was then inoculated to the culture medium at the rate of one inoculating loopful per flask and was subjected to aerated-stirring culture at 55° C. for 120 hours. A supernatant (2.2 l) which had been obtained by subjecting the cultured broth to centrifugation after completion of the culture applied to a column of SEPABEADS FP-DA13 (Mitsubishi Kasei Corp., 5 cm×20 cm) equilibrated with 10 mM phosphate buffer (pH 7.2). After the column was washed first with the above buffer and then with the above buffer containing 0.3M of potassium chloride, the β-galactosyltransferase was eluted with the above buffer which contained 0.5M of potassium chloride. Active fractions were concentrated by ultrafiltration and then dialyzed against 10 mM phosphate buffer (pH 7.2).

EXAMPLE 2

The inner dialyzate was applied to a column of DEAE-Sepharose CL-6B (product of Pharmacia AB, 2.8 cm×20 cm) which had been equilibrated with 10 mM phosphate buffer (pH 7.2). After the column was washed first with the above buffer and then with the above buffer containing 0.2M of potassium chloride, the column was subjected eluted by linear concentration gradient of from 0.2M potassium chloride to 0.6M potassium chloride (total volume: 400 ml) so that β-galactosyltransferase was eluted. After active fractions were concentrated by ultrafiltration, the concentrate was loaded in several portions in a "TSK Gel G3000SW-XL" (TOSOH CORP.) which had been equilibrated with 10 mM phosphate buffer (pH 7.2) containing 0.15M of potassium chloride (flow rate: 1.0 ml/min; detection: absorbance at 280 nm). Active fractions were concentrated by ultrafiltration and then dialyzed against 10 mM phosphate buffer (pH 7.2).

Purified β-galactosyltransferase obtained from the above had 240 pNPGU of an amount activity and 10 pNPGU/mg of comparative activity.

EXAMPLE 3

Lactose (5 g) was dissolved in 0.05M acetate buffer (pH 6.0) to give the volume of 10 ml, to which the β-galactosyltransferase 10 pNPGU obtained in Example 1 was added. They were then reacted at 65° C. for 4 hours. The reaction mixture was treated at 95° C. for 5 minutes to terminate the reaction. A portion of the reaction mixture was diluted tenfold. By analyzing it by high-performance chromatography with a column of Shodex Ionpack KS801 (mobile phase: water; column temperature: 70° C.; flow rate: 1 ml/min; detector: differential refractometer), the saccharide composition of the reaction mixture was determined. The reaction mixture contained 7% of tetra- or higher saccharides, 21% of trisaccharides, 48% of disaccharides and 24% of monosaccharides, all by wt.% based on the whole saccharides.

EXAMPLE 4

Five grams of the enzyme immobilizing matrices "FE4612" (product of Japan Organo Co., Ltd.) were stirred at 50° C. for 2 hours in 4% NaOH and then washed with deionized water. The carrier was suspended in 15 ml of 5% glutaraldehyde, followed by stirring for 1 hour. The carrier was then washed with 10 mM phosphate buffer, suspended in 10 mM phosphate buffer containing 1,000 U of the enzyme, and then stirred for 2 hours to immobilize the same. The matrices were washed with 10 mM of phosphate buffer. It was used to provide an immobilized β-galactosyltransferase. The activity yield at the immobilization was 87%. One gram of the immobilized β-galactosyltransferase was suspended in 100 ml of 0.05M acetate buffer (pH 6.0) which contained 60% (w/v) of lactose. The suspension was stirred at 65° C. for 24 hours, whereby a reaction was performed. A portion of the reaction mixture was diluted tenfold. By analyzing it by high-performance chromatography with a column of Shodex Ionpack KS801 (mobile phase: water; column temperature: 70° C.; flow rate: 1 ml/min; detector: differential refractometer), the saccharide composition of the reaction mixture was determined. The reaction mixture contained 3% of tetra- or higher saccharides, 25% of trisaccharides, 58% of disaccharides and 14% of monosaccharides, all by wt. % based on the whole saccharides. Taking the above reaction as 1 cycle, it was repeated. Assuming that the half-life of the activity of the immobilized β-galactosyltransferase is governed by a first-order reaction, the half-life was determined by calculation. The half-life of the activity of the immobilized β-galactosyltransferase was determined to be at least 300 cycles.

EXAMPLE 5

Four cell strains, i.e., Thermomonospora sp. SAM 1546, Thermomonospora sp SAM 1547, Thermoactinomyces sp. SAM 1544 and Thermoacrinomyces sp. SAM 1545 were separately subjected to shaking culture at 55° C. for 4 days in 500-ml flasks each of which contained 100 ml of a culture medium (pH 7.2) containing 3% of lactose, 0.2% of peptone, 0.02% of yeast extract, 0.2% of $KH_2PO_4$, 0.3% of NaCl and 0.01% of $MgSO_4 \cdot H_2O$, whereby β-galctosyltransferase samples were obtained, respectively.

The thus-obtained β-galactosyltransferase samples had the properties shown in Table 4.

TABLE 4

| Characteristics | Thermomonospora s.p. SAM1546 | Thermomonospora s.p. SAM1547 | Thermoactinomyces s.p. SAM1544 | Thermoactinomyces s.p. SAM1545 |
|---|---|---|---|---|
| (Action) | | | | |
| Transfer reaction[1] | + | + | + | + |
| Hydrolysis | + | + | + | + |
| (Substrate specificity of hydrolysis) | | | | |
| Lactose[2] | + | + | + | + |
| p-Nitrophenyl-β-galactoside[3] | + | + | + | + |
| p-Nitrophenyl-α-galactoside[4] | − | − | − | − |
| Optimal pH[5] | 6.0–7.5 | 6.0–7.5 | 6.0–7.5 | 6.0–7.5 |
| pH stability[6] | 5–8 | 5–8 | 5–8 | 5–8 |
| Heat stability[7] | About 82% | About 82% | About 88% | About 88% |

Note:
+: Catalyzes.
−: Does not catalyze.
[1] Reacted at 55° C. for 240 minutes in 10 mM phosphate buffer (pH 7.2) containing 1 mM lactose.
[2] Reacted at 55° C. for 10 minutes in 10 mM phosphate buffer (pH 7.2) containing 10 mM lactose.
[3] Reacted at 55° C. for 5 minutes in 10 mM phosphate buffer (pH 7.2) containing 10 mM p-nitrophenyl-β-galactoside.
[4] Reacted at 55° C. for 5 minutes in 10 mM phosphate buffer (pH 7.2) containing 10 mM p-nitrophenyl-α-galactoside.
[5] Reacted at 55° C. for 5 minutes in 10 mM acetate buffer (pH 4.0–6.5) or phosphate buffer (pH 6.0–8.5) containing 10 mM p-nitrophenyl-β-galactoside.
[6] Ice-cooled immediately after incubation at 55° C. for 15 minutes in 10 mM acetate buffer (pH 4.0–6.5) or phosphate buffer (pH 6.0–8.5). Residual activity was determined by measurement under the above conditions 3).
[7] Ice-cooled immediately after incubation at 60° C. for 1 hour in 10 mM acetate buffer (pH 7.2). Residual activity was determined by measurement under the above conditions 3).

EXAMPLE 6

The lactase ("Lactase Y-A0", trade name; product of YAKULT HONSHA CO., LTD.) derived from *Aspergillus oryzae*, the lactase ("Biolacta", trade mark; product of Daiwa Kasei K.K.) derived from *Bacillus circulans* and the β-galactosyltransferase of the present invention were separately dissolved in 0.01M phosphate buffer (pH 7.0) to prepare 0.1 mg/ml enzyme solutions. After the respective enzyme solution were incubated at 60° C. for 1 hour, they were immediately ice-cooled. The residual activities of the respective enzymes were then measured in accordance with the optimal conditions described on their use instructions. As a result, the residual activities of the lactase derived from *Aspergillus oryzae*, the lactase derived from *Bacillus circulans* and the β-galactosyltransferase of the present invention were 1%, 1% and 96%, respectively.

EXAMPLE 7

β-Galactosyltransferases which had been obtained from cultures of Thermomonospora sp. SAM 1546, Thermomonospora sp. SAM 1547, Thermoacrinomyces sp. SAM 1544 and Thermoactinomyces sp SAM 1545, respectively, were separately added in an amount of 1 pNPGU to portions of a solution of 0.5 g of lactose in 0.05M acetate buffer (pH 6) to give final volumes of 1.0 ml. They were separately reacted at 65° C. for 8 hours.

The reaction mixtures were treated at 95° C. for 5 minutes to terminate the reactions. Portions of the reaction mixtures were diluted tenfold and were then analyzed by high-performance chromatography with a column of Shodex Ionpack KS-801 (mobile phase: water; column temperature: 70° C.; flow rate: 1 ml/min; detector: differential refractometer), so that the saccharide compositions of the reaction mixtures were determined.

As a result, irrespective of the source for the β-galactosyltransferase used, the resultant reaction mixture contained 3–7% of tetra- or higher saccharides, 18–21% of trisaccharides, 48–52% of disaccharides and 21–26% of disaccharides, all wt.% based on the whole saccharides.

EXAMPLE 8

Production of lactose-decomposed milk containing galactooligosaccharide by the use of β-galactosyltransferase of *Saccharopolyspora rectivirgula*:

Cow milk (lactose content: 4.8%, nonfat milk solids content: 8.3%) was heated to 60° C., to which β-galactosyltransferase obtained from *Saccharopolyspora rectivirgula* was added in an amount of 16–24 LU per gram of lactose. They were reacted for 4–7 hours. Then, by high-performance liquid chromatography with a column of Shodex Ionpack KS801 (mobile phase: water; column temperature: 70° C.; flow rate: 1.0 ml/min; detector: differential refractometer), the saccharide composition of the cow milk after the above treatment was analyzed. The results are shown in Table 5. Incidentally, the lactose hydrolyzing activity of the galactosyltransferase remained substantially 100% even after the above reaction.

TABLE 5

| | Treatment conditions (Amount of enzyme added, reaction time) | | |
|---|---|---|---|
| | Untreated | 16 LU/g-lactose 7 hr | 24 LU/g-lactose 4 hr |
| Saccharide composition (% based on whole saccharides) | | | |
| Oligosaccharides of trisaccharides and higher | 0.0% | 10.7% | 11.4% |
| Disaccharides | 100.0 | 23.3 | 24.8 |
| Monosaccharides | 0.0 | 66.0 | 63.9 |

EXAMPLE 9

The stability of the β-galactosyltransferase obtained from Saccharopolyspora rectivirgula in cow milk in the production of lactose-decomposed milk containing galactooligosaccharide was investigated in further detail.

Portions of cow milk (lactose content: 4.8%, non-fat milk solids content: 8.3%) were heated to 60° C., 65° C.

and 70° C., respectively, to which the β-galactosyltransferase of *Saccharopolyspora rectivirgula* was added in an amount of 24 pNPGU per ml of the cow milk to initiate a reaction. To determine the residual activity of the enzyme in the reaction, portions (0.02 ml) of the reaction mixtures were sampled 1, 2, 4 and 8 hours after the initiation of the reaction and were added to 1.0 ml-portions of cow milk. They were reacted at 60° C. for 1 hour, during which the rates of decrement of lactose in the portions of cow milk were measured, respectively. For the same of comparison, a similar experiment was also conducted with respect to the β-galactosidase ("Biolacta", trade mark; product of Daiwa Kasei K.K.) of *Bacillus circulans*. The results are summarized in Table 6.

TABLE 6

| Treatment temp. (°C.) | Treatment time (hr) | Residual activity of enzyme | |
|---|---|---|---|
| | | S. rectivirgula | B. circulans |
| 60 | 0 | 100 | 100 |
| | 1 | 100 | 77 |
| | 2 | 100 | 79 |
| | 4 | 100 | 76 |
| | 8 | 100 | 71 |
| 65 | 0 | 100 | 100 |
| | 1 | 100 | 39 |
| | 2 | 100 | 15 |
| | 4 | 100 | 0 |
| | 8 | 100 | 0 |
| 70 | 0 | 100 | 100 |
| | 1 | 90 | 3 |
| | 2 | 80 | 0 |
| | 4 | 60 | 0 |
| | 8 | 11 | 0 |

EXAMPLE 10

Portions of the heat-resistant β-galactosyltransferase were dialyzed overnight at 4° C. against buffers A and B, respectively. After a further portion of the heat-resistant β-galactosyltransferase was incubated at 4° C. for 1 hour in the presence of ethylenediamine tetraacetate (EDTA; final concentration: 1 mM), the resultant mixture was dialyzed overnight at 4° C. against buffer C.

The respective inner dialyzates were separately heated at 60° C. for 5, 10, 30, 60, 120 and 240 minutes. At the end of each heat treatment time, the thus-treated inner dialyzates were sampled in a predetermined amount and immediately ice-cooled. Using p-nitrophenyl-β-D-galactopyranoside as a substrate, the residual activities of the enzyme were measured by the method described above under "Enzymochemical properties (9)".

Incidentally, buffer C is 0.01M phosphate buffer (pH 7.2), while buffers A and B are the same as buffer C except for the inclusion of 20 μM of $MnCl_2$ and 20 μM of $ZnCl_2$, respectively.

The results so obtained are diagrammatically shown in FIG. 1.

We claim:

1. A process for the production of a novel β-galactosyltransferase, which comprises culturing a microorganism belonging to the family of Actinomycetaceae and produces a β-galactosyltransferase having the following physicochemical properties:

(1) Action

Transfer reaction: Forms 1 mole of a β-D-galactopyranoside Gal-Y and 1 mole of X from 1 mole of another β-D-galactopyranoside Gal-X and 1 mole of a galactosyl group receptor, Y wherein X and Y are both compounds other than water and are each a saccharide or aglycon, Hydrolysis: Forms 1 mole of X and 1 mole of galactose by hydrolyzing 1 mole of the β-D-galactopyranoside Gal-X, (2) Substrate specificity Hydrolyzes lactose and p-nitrophenyl-β-D-galactopyranoside but does not hydrolysed p-nitrophenyl-α-D-galactopyranoside, (3) Optimal pH
   5.0–8.0, (4) pH Stability Stable at pH 5–8 (both inclusive) when treated at 55° C. for 15 minutes, (5) Heat Stability Retains at least 80% of its initial activity even after incubated at 60° C. for 1 hours in 0.01M phosphate buffer (pH 7.2) or at least 80% of its initial activity even after incubated at 65° C. for 24 hours in the same buffer (6) containing at least 1M of lactose having a molecular weight of 140,000±20,000, as a monomer subunit as determined by SDS polyacrylamide gel electrophoresis and isolating and collecting the β-galactosyltransferase from the resultant culture.

2. The process of claim 1, wherein the microorganism belonging to the family of Actinomycetaceae and capable of producing the novel β-galactosyltransferase is a microorganism belonging to the genus Saccharopolyspora, the genus Thermomonospora or the genus Thermoactinomyces.

* * * * *